(12) United States Patent
Bergeron, Jr.

(10) Patent No.: US 6,258,931 B1
(45) Date of Patent: Jul. 10, 2001

(54) DEOXYHYPUSINE REAGENT AND PEPTIDES

(75) Inventor: Raymond J. Bergeron, Jr., Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 09/136,493

(22) Filed: Aug. 19, 1998

(51) Int. Cl.⁷ .............................. C07K 7/00; C07K 14/00; C07C 51/00; C07C 229/02
(52) U.S. Cl. .................. 530/324; 530/325; 530/326; 530/327; 530/329; 530/330; 530/333; 560/155; 560/159; 514/12; 514/13; 514/17; 514/18
(58) Field of Search ................................. 530/327, 329, 530/330, 333, 324, 325, 326; 514/14, 17, 18, 12, 13; 560/155, 159

(56) References Cited

PUBLICATIONS

Bergeron, et al., "Total Syntheses of (+) –Hypusine and Its (2S,9S) –Diastereomer", *J.Org.Chem.*, vol.58, pp. 6804–6806 (1993).
Bergeron, et al., "Development of a Hypusine Reagent for Peptide Synthesis", *J.Org.Chem.*, vol. 62, pp. 3285–3290 (1997).
Knapp, S., et al. "Synthesis of Hypusine and Other Polyamines Using Dibenzyltriazones for Amino Protection" *J.Org.Chem.*, vol. 57, pp. 6239–6256 (1992).
Mehta, A., et al., "Improved Efficiency and Selectivity in Peptide Synthesis: Use of Triethylsilane as a Carbocation Scavenger in Deprotection of t–Butyl Esters and t–Butoxycarbonyl—Protected Sites", *Tetrahedron Lett.*, vol. 33, pp. 5441–5444 (1992).
Sumimoto, H., et al. "Polymerization of β–Cyanopropionaldehyde", *J.Polym.Sci.*, vol. 4, pp. 907–916 (1966).
Abbruzzese, et al., "Inhibition of DexoyhypusineHydroxylase by Polyamines and by a Deoxyhypusine Peptide." 1989, 997, 248–255.*
Grant, G., "Synthetic Peptides: A User'Guide" W.H. Freeman and Company:New York, 1992, Chapter 3.*
Park et al., "Comparison of the Activities of Variant Forms of eIF–4D: The Requirement for Hypusin Deoxyhypusine," The Journal of Biological Chemistry, 266(13) :7988–7994 (1991).

* cited by examiner

*Primary Examiner*—Michael P. Woodward
*Assistant Examiner*—Anish Gupta
(74) *Attorney, Agent, or Firm*—Cooley Godward LLP; Alexandra J. Baran (57) ABSTRACT

The invention relates to a method and reagent for the synthesis of peptides containing deoxyhypusine, the reagent having the formula:

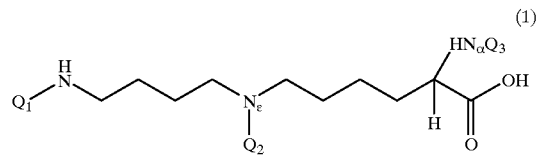

(1)

wherein:
Q₁ and Q₂ may be the same or different and are amino protective groups,
and Q₃ is an amino protective group which is orthogonal to Q₁ and Q₂.

The invention also relates to peptides of formula

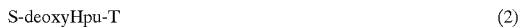

S-deoxyHpu-T (2)

that may be synthesized using the reagent of the invention, wherein deoxyHpu is the deoxyhypusine residue, S and T are each independently peptide residues from zero to 12 amino acids in length.

17 Claims, 2 Drawing Sheets

SEQUENCE LISTING

<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: conserved
      region
<220> FEATURE:
<221> NAME/KEY: SITE
<222> LOCATION: (7)
<223> OTHER INFORMATION: Hypusine

<400> SEQUENCE: 1

Ser Thr Ser Lys Thr Gly Xaa His Gly His Ala Lys
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: example of
      peptides of the invention
<220> FEATURE:
<221> NAME/KEY: SITE
<222> LOCATION: (7)
<223> OTHER INFORMATION: Deoxyhypusine

<400> SEQUENCE: 2

Ser Thr Ser Lys Thr Gly Xaa His Gly His Ala Lys
 1               5                  10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: example of
      peptides of the invention
<220> FEATURE:
<221> NAME/KEY: SITE
<222> LOCATION: (4)
<223> OTHER INFORMATION: Deoxyhypusine

<400> SEQUENCE: 3

Cys Thr Gly Xaa His Gly
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: example of
      peptides of the invention
<220> FEATURE:
<221> NAME/KEY: SITE
<222> LOCATION: (3)
<223> OTHER INFORMATION: Deoxyhypusine

<400> SEQUENCE: 4

Thr Gly Xaa His Gly
 1               5

<210> SEQ ID NO 5
<211> LENGTH: 6

```
<212> TYPE: PRT
<213> ORGANISM: Artificial Sequence
<220> FEATURE:
<223> OTHER INFORMATION: Description of Artificial Sequence: example of
      peptides of the invention
<220> FEATURE:
<221> NAME/KEY: SITE
<222> LOCATION: (4)
<223> OTHER INFORMATION: Deoxyhypusine

<400> SEQUENCE: 5

Lys Thr Gly Xaa His Gly
  1               5

<210> SEQ ID NO 6
<211> LENGTH: 8
<212> TYPE: PRT
<213> ORGANISM: Homo sapiens
<220> FEATURE:
<221> NAME/KEY: SITE
<222> LOCATION: (3)
<223> OTHER INFORMATION: Hypusine

<400> SEQUENCE: 6

Thr Gly Xaa His Gly His Ala Lys
  1               5
```

DEOXYHYPUSINE REAGENT AND PEPTIDES

FIELD OF THE INVENTION

The present invention relates to a novel deoxyhypusine derivative useful as a reagent for synthesizing peptides containing deoxyhypusine. The invention further relates to those peptides synthesized using the reagent.

BACKGROUND OF THE INVENTION

DESCRIPTION OF THE PRIOR ART

Hypusine, [(2S,9R)-2,11-diamino-9-hydroxy-7-azaundecanoic acid] or [$N_\epsilon$-(4-amino-2-hydroxybutyl)lysine], an unusual naturally occurring amino acid, having the structure:

(A)

was first isolated from bovine brain extracts by Shiba et al. in 1971 [*Biochim. Biophys. Acta.*, Vol. 244, pages 523–531 (1971)]. The molecule has two chiral centers, one at position 2 and one at position 9, each of which can be classified R or S by the Cahn-Ingold-Prelog method. The (2S,9R)-diastereomer (B), formed as a post-translational (B)

modification of lysine, has been shown to occur on a precursor protein of the eukaryotic initiation factor "eIF-5A" (formerly called eIF-4D; the nomenclature for initiation factors having been revised) [Cooper et al., *Proc. Natl. Acad. Sci. USA*, Vol. 80, pages 1854–1857 (1983); and Safer, *Eur. J. Biochem.*, Vol.186, pages 1–3 (1989)]. Deoxyhypusine, [2,11-diamino-7-azaundecanoic acid], has the following chemical structure:

(C)

The naturally occurring form has a chiral center at the 2-position in the (S) configuration.

The 17-kDa protein eIF-5A seems to be very highly conserved amongst many eukaryotic species including yeast and higher mammals, attesting to its importance from an evolutionary perspective. [Wohl, T., et. al., *Mol. Gen. Genet.*, Vol. 241, 305–311 (1993); Magdolen, V. et al., *Mol. Gen. Genet.*, Vol. 244, 646–652 (1994)]. In particular, the 12-amino acid region surrounding the hypusine residue, L-Ser-L-Thr-L-Ser-L-Lys-L-Thr-Gly-Hpu-L-His-Gly-L-His-L-Ala-L-Lys, SEQ ID NO:1 is extremely well-conserved across species. [Bartig, D. et al., *Eur. J. Biochem.*, Vol. 204, 751–758 (1992)]. Hypusination of eIF—5A, or "maturation" of this protein, occurs as a post-translational event. [Park, M. H. et al., *J. Biol. Chem.*, Vol. 257, 7217–7222 (1982)]. An aminobutyl group is first removed from spermidine and attached to Lys-50 of the human protein via deoxyhypusine synthase. [Park, M. H.; Wolff, E. C.; Abbruzzese, A.; Folk, J. E., *Adv. Exp. Med. Biol.* Vol. 250, 435–447 (1988); Wolff, E. C.; Park, M. H.; Folk, J. E. *J. Biol. Chem.*, Vol. 265, 4793–4799 (1990)]. Next, deoxyhypusine hydroxylase introduces the hydroxyl group at C-9 in the (R-) configuration [Park (1982)].

In the mid-1970's, eIF-5A was shown to stimulate ribosomal subunit joining and to enhance 80 S-bound Met-t-RNA reactivity with puromycin [Anderson et al., *FEBS Lett.*, Vol. 76, pages 1–10 (1977); and Kemper et al., *J. Biol. Chem.*, Vol. 251, pages 5551–5557 (1976)]. Later, in 1983, Cooper et al., supra, suggested that a hypusine-modified protein serves as an important initiation factor in all growing eukaryotic cells. In 1986, Park et al. [*J. Biol. Chem.*, Vol. 261, pages 14515–14519 (1986)] isolated the eIF-5A protein from human red blood cells and elucidated the amino acid sequence surrounding the single hypusine residue, as Thr-Gly-Hpu-His-Gly-His-Ala-Lys. SEQ ID NO:6. In addition, because of the potential application to the control of HIV replication [Bevec et al., *J. Proc. Natl. Acad. Sci. USA*, Vol. 91, pages 10829–10833 (1994); and Ruhl et al. *J. Cell Biol.*, Vol. 123, pages 1309–1320 (1994)], the synthesis of eIF-5A analogues is of great therapeutic significance.

The inhibitor of deoxyhypusine synthase, $N^1$-guanyl-1,7-diaminoheptane ($CG_7$), inhibits the growth of CHO cells without affecting polyamine metabolism. [Park, M. H., et al., *J. Biol. Chem.*, Vol. 269, 27827–27832 (1994)]. Site-directed mutagenesis experiments in which Lys-50 was replaced with arginine resulted in a nonfunctional protein in yeast cells; the arginine could not be modified to form hypusine [Schnier, J, et al., *Mol. Cell. Biol.*, Vol. 11, 3105–3114 (1991)]. Furthermore, yeast cells that had the wild-type copy of the gene replaced with the mutant copy failed to grow. The precise role of the hypusine residue in eIF-5A activity remains elusive. While it is clear that the N-terminal methionine of the protein is replaced with an acetyl group, and that acetylation occurs at Lys-47, neither event seems critical to the protein's function [Klier, H. et al., *FEBS Lett.* Vol. 334, 360–364 (1993); Klier, H., et al., *Biochemistry*, Vol. 34, 14693–14702 (1995)].

Probably the most intriguing aspect regarding eIF-5A is its role in the replication of human immunodeficiency virus (HIV); eIF-5A is a transactivating factor during replication of HIV. [Ruhl, M., et al., *J. Cell Biol.*, Vol.123, 1309–1320 (1993)]. The eIF-5A molecule binds to a complex formed between the Rev Response Element (RRE) in the Stem-Loop IIB of the viral mRNA and Rev, a viral protein that serves as a nuclear export signal. [Ruhl et al., supra]. Once eIF-5A binds to Rev-RRE, the now active eIF-5A-Rev-RRE complex is able to be exported from the nucleus; viral replication ensues. In experiments in which antisense nucleotides were used to prevent eIF-5A synthesis, viral replication was inhibited. [Gerace, L., *Cell*, Vol. 82, 341–344 (1995).] It has also been demonstrated in gel shift experiments that the hypusine- or deoxyhypusine-containing fragments were required for this binding of eIF-5A to Rev-RRE. In keeping with these observations, two issues become particularly intriguing. Bevec et al. have shown that Rev has domains which direct both nuclear import and nuclear export. Certain eIF-5A mutants, while capable of being transported into the nucleus and binding to Rev-RRE, actu- ally prevent nuclear export and, thus, viral replication. [Bevec, D., et al., *Science,* Vol. 271,1858–1860 (1996); Junker, U.; et al., *Hum. Gene Ther.,* Vol. 7, 1861–1869 (1996)].

The observations that eIF-5A is required for both mitotic events and HIV viral replication and that immature eIF-5A must be deoxyhypusinated or hypusinated for activity render inhibition of eIF-5A deoxyhypusination or hypusination an interesting target in therapeutic strategies for anticancer and antiviral drug development. Another potential antiviral strategy involves identifying the basic platform within eIF-5A responsible for nuclear import that will permit Rev-RRE binding but not nuclear export of viral message.

In order to study the above-described biochemical events and to develop therapeutic strategies for anticancer and antiviral drug development, there is a need for synthetic methodology for accessing model peptides containing hypusine and deoxyhypusine. A reagent and method for producing peptides incorporating hypusine are disclosed in a co-pending application, U.S. Ser. No. 09/136,270, entitled "Hypusine Reagent for Peptide Synthesis," filed on Aug. 19, 1998, as a continuation-in-part application of U.S. Ser. No. 08/962,300, filed Oct. 31, 1997, which disclosure is incorporated herein by reference. Novel peptides incorporating hypusine produced via the method of the present invention are disclosed in a co-pending application, U.S. Ser. No. 09/136,472,entitled "Hypusine Peptides," filed on Aug. 19, 1998, as a continuation-in-part application of U.S. Ser. No. 08/975,656, filed Nov. 21, 1997, which disclosure is incorporated herein by reference. The hypusine reagent and peptides are also disclosed in Bergeron, R. J. et al., *J. Org. Chem.,* Vol. 62, 3285–3290 (1997), which disclosure is incorporated herein by reference. It is an object of the present invention to provide novel peptides incorporating deoxyhypusine and a reagent and method for their synthesis.

SUMMARY OF THE INVENTION

The present invention provides a derivative of deoxyhypusine useful as a reagent for synthesizing peptides containing deoxyhypusine, the derivative having the formula:

wherein:

Q$_1$ and Q$_2$ may be the same or different and are amino protective groups
and Q$_3$ is an amino protective group which is orthogonal to Q$_1$ and Q$_2$.

An additional embodiment of the invention relates to a method for synthesizing a deoxyhypusine reagent as defined above comprising:

a. providing an ester of N$_\epsilon$-, N$_\alpha$-diprotected lysine, the ester having the formula:

wherein prot and prot' are N-protective groups which are mutually orthogonal and R is the residue of an esterifying alcohol which is orthogonal with respect to prot and prot', b. removing prot from N$_\epsilon$ of (a) and converting the product to a compound of the formula:

c. condensing (b) with 3-cyanopropanal and reducing the intermediate imine to a cyanide of the formula:

d. reducing (c) to produce a triamine of the formula:

e. protecting the free amino groups of (d) to produce an ester of the formula:

f. removing R and prot' from (e) to produce a compound of the formula:

and g. acylating the free amino group to produce the deoxyhypusine derivative

The reduction in steps (c) and (d) may optionally be carried out in one reaction.

A further embodiment of the invention relates to compounds of structure (2)

S-deoxyHpu-T (2)

which may be synthesized using the reagent of the invention, wherein deoxyHpu is the deoxyhypusine amino acid residue, S and T are each independently peptide residues from zero to about 12 amino acids in length. Compounds of the invention find utility in the study of biochemical processes involving hypusine and deoxyhypusine.

DETAILED DESCRIPTION OF THE INVENTION

In the preceding and subsequent descriptions of the present specification, suitable examples and illustrations of the various definitions which the present invention includes within the scope thereof are explained in detail as follows.

The expression "amino protective group" as used herein is intended to designate groups ($Q_1$, $Q_2$ and $Q_3$) which are inserted in place of a hydrogen atom of an amino group or groups in order to protect the amino group(s) during synthesis.

Selection of a suitable amino protecting group will depend upon the reason for protection and the ultimate use of the protected product. When the protecting group is used solely for protection during synthesis, then a conventional amino protecting group may be employed. Appropriate amino protecting groups are known in the art and are described, for example, by Bodanszky in *Principles of Synthesis*, Springer-Verlag, New York (1984); by Ives in U.S. Pat. No. 4,619,915; and in the various publications on peptide chemistry referred to in the latter. See also *Methoden der Organischen Chemie*, Houben-Weyl, Vol. 15, No. 1, for protecting groups and Vol. 15, No. 2, for methods of peptide synthesis. Representative amino protecting groups for synthetic use include acyl groups such as tert-butoxycarbonyl, benzyloxycarbonyl, fluorenylmethoxycarbonyl (FMOC), benzoyl, acetyl and the like. Yet other conventional amino protecting groups for use in synthesis are described in the literature [Bodanszky, supra, and Ives, supra].

The term "orthogonal" when used herein to modify the term "protective group(s)" is intended to designate those protective groups in the molecule which are capable of being selectively removed from the molecule in the presence of other protective groups in the molecule without affecting the latter.

The various protecting groups for amino functions discussed above can be substituted for the amino functions in the instant amino acids/peptides (or their precursor molecules) by methods well known in the art. Methods for chemical removal of the protecting groups (when such are not to be retained in the pharmaceutically useful end product) are likewise well known to the skilled artisan. Typically, amine protecting groups are chemically removed by acidolysis (acid hydrolysis) or hydrogenation, depending on the particular protecting group employed. Carboxyl protecting groups are typically removed chemically by acid or base hydrolysis. Protecting groups which are incorporated in the pharmaceutical end product must be amenable to hydrolytic or metabolic cleavage in vivo.

The deoxyhypusine reagent of the present invention is useful as a synthon for accessing peptides, in particular, a deoxyhypusine analogue of the eIF-5A pentapeptide sequence. Thus, peptides incorporating deoxyhypusine may be prepared by sequential addition to an amino acid or protected amino acid, or the addition of the reagent to an amino terminus free peptide. Thus, the reagent can be inserted directly into a dipeptide or larger fragment in the course of the peptide synthesis. At any point in the synthesis, the α-nitrogen protecting group of the deoxyhypusine reagent can be removed and the carboxylate group of an amino acid, a protected amino acid, or a carboxylate free peptide coupled to it. Methods for sequential addition of amino acids to form peptides, utilizing protecting groups where appropriate, are well known in the art. An excellent summary of such methods, including both solid phase synthesis and synthesis in solution, is contained in U.S. Pat. No. 4,530,920 (Nestor et al.) which is relied upon and incorporated by reference herein in its entirety. See also *Solid Phase Peptide Synthesis,* second edition, John Morrow Stewart and Janis Dillaha Young, eds., Pierce Chemical Company, Rockford, Ill. (1984). Peptides provided by the present invention can also be prepared by segment condensation methods described in the prior art [Bodanszky, supra, and *Methoden der Organischen Chemie,* supra].

In compounds of structure (2), S and T are peptide residues from zero to about 12 amino acids in length, and preferably, are peptide residues from zero to about six amino acids in length. Most preferably, S and T are peptide residues from zero to about three amino acids in length. S and T may vary independently in length and in composition of amino acid residues. Non-limiting examples of peptides of the invention are:

L-Ser-L-Thr-L-Ser-L-Lys-L-Thr-Gly-deoxyHpu-L-His-Gly-L-His-L-Ala-L-Lys, (SEQ ID NO:2)

L-Cys-L-Thr-Gly-deoxyHpu-L-His-Gly,(SEQ ID NO:3) deoxyHpu-L-His-Gly,

L-Thr-Gly-deoxyHpu-L-His-Gly,(SEQ ID NO:4)

L-Lys-L-Thr-Gly-deoxyHpu-L-His-Gly,(SEQ ID NO:5)

wherein the deoxyHpu linkage is the 2(S)-isomer or the 2(R)-isomer thereof. Where deoxyhypusine is in the 2(R)-configuration, the compounds of the invention are generated from the appropriately configured lysine starting material.

Compounds of the invention find utility in the study of biochemical processes involving hypusine and deoxyhypusine, such as in the study of transport mechanisms for eIF5A and in interfering with the formation of a functional eIF5A-Rev-RRE complex, which would, in turn, hinder the nuclear export of such a complex.

Figure 1:
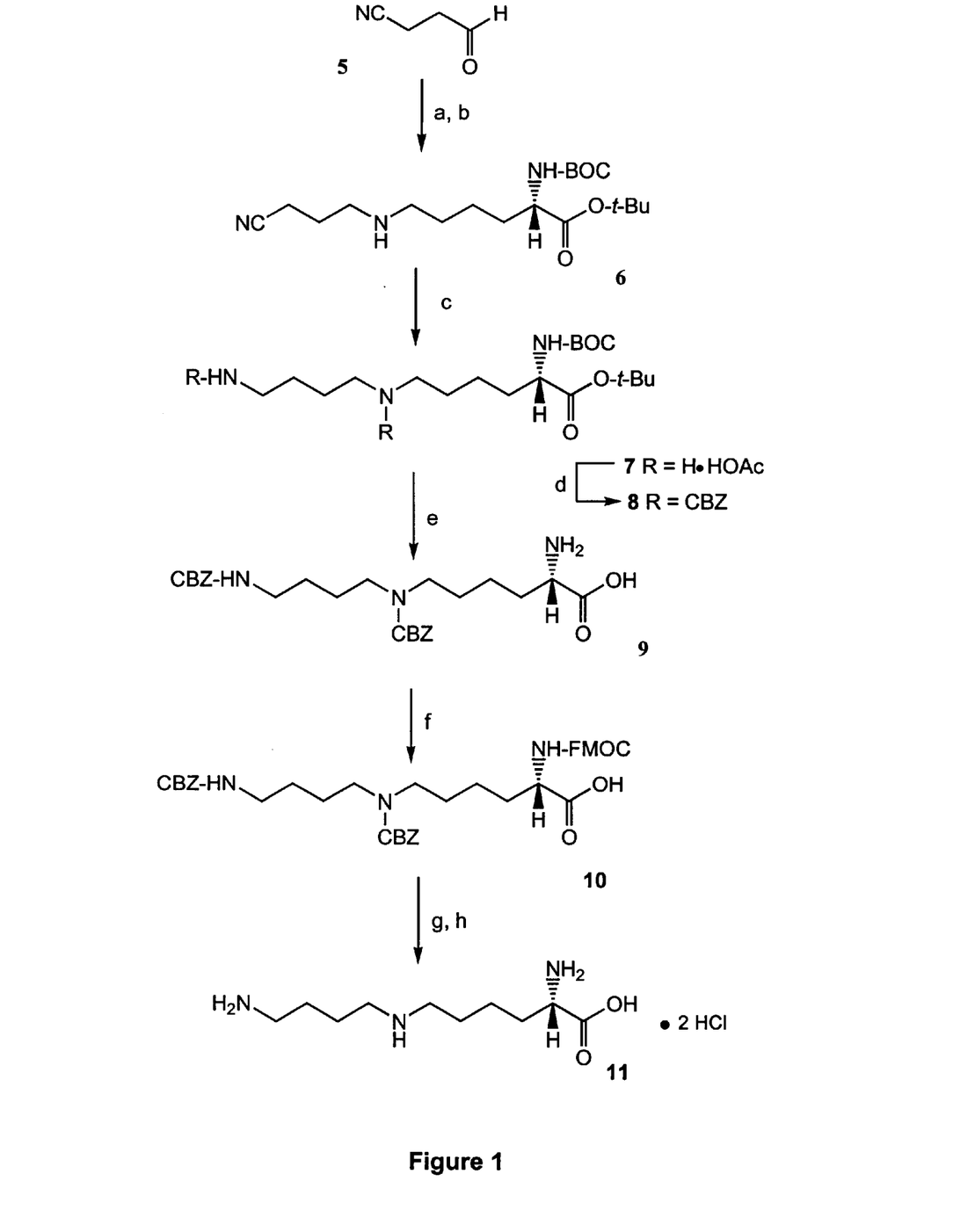
FIG. 1 is a depiction of a reaction scheme for synthesizing an example of the deoxyhypusine reagent of the invention and free deoxyhypusine. Reagents: (a) $N_\alpha$-BOC-$N_\epsilon$-CBZ-L-lysine tert-butyl ester, benzene, molecular sieves; (b) $H_2$, $PtO_2$, THF; (c) $H_2$, Pd/C, $PtO_2$, HOAc; (d) CBZ-ONSu, $KHCO_3$; (e) TFA, triethylsilane, $CH_2Cl_2$; (f) FMOC-ONSu, $Na_2CO_3$; (g) piperidine; (h) HBr/HOAc in TFA, phenol, pentamethylbenzene, triisopropylsilane.

A specific example of the synthesis of the deoxyhypusine reagent 10 is shown in FIG. 1. The initial step involves a molecular sieve-promoted condensation of 3-cyanopropanal 5 (Sumimoto, H.; Kobayashi, K., *J. Polym. Sci.,* Vol. 4, 907–916 (1966)] with the Nα-BOC-tert-butyl ester of L-lysine (4) and reduction of the resulting intermediate imine over $H_2/PtO_2$ [Knapp, S.; Hale, J. J.; Bastos, M.; Molina, A.; Cheil, K. Y., *J. Org. Chem.*, Vol. 57, 6239–6256 (1992)] to the deoxyhypusine framework 6. This nitrile on 6 was further reduced using $H_2$ over Pd/C and $PtO_2$ in acetic acid to 8; the N-7 and N-12 positions were reacted with CBZ-ONSu to produce tetraprotected deoxyhypusine 8. Both tert-butyl protecting groups were removed with trifluoroacetic acid and triethylsilane [Mehta, A.; Jaouhari, R.; Benson, T. J.; Douglas, K. T., *Tetrahedron Lett.*, Vol. 33, 5441–5444 (1992)], and the amino acid 9 was converted to the Nα-FMOC-di-CBZ-protected compound 10. This reagent was both deprotected to yield free deoxyhypusine and utilized to generate a deoxyhypusine-containing hexapeptide.

For free deoxyhypusine dihydrochloride (11), the deoxyhypusine reagent 10 was first treated with piperidine to remove the FMOC protecting group and then deprotected using 30% HBr in trifluoroacetic acid with a cocktail of cation scavengers (FIG. 1). Once the reaction was complete, the reactants were dissolved in water, and the non-salts were extracted into methyl tert-butyl ether. After concentration, the product was chromatographed on silica, eluting with methylene chloride/methanol/ammonium hydroxide. The free amine was converted to the dihydrochloride salt 11. Analytical data of the final compound were in agreement with the literature values [Knapp, S.; Hale, J. J.; Bastos, M.; Molina, A.; Cheil, K. Y., *J. Org. Chem.*, Vol. 57, 6239–6256 (1992)].

Deoxyhypusine reagent molecules of differing stereochemistries may be obtained in a like manner by employing starting materials of opposite sterochemistries, for example, by using D-lysine.

The deoxyhypusine reagent was utilized to prepare Cys-Thr-Gly-deoxyhypusine-His-Gly. The synthesis of the hexapeptide 13 (FIG. 2) was performed on a 2-chlorotrityl resin using SPPS and FMOC chemistry with HBTU as an activating agent. The cysteine and histidine residues of the hexapeptide were protected as 4-methoxytrityl-(Mmt) and 4-methyltrityl-groups (Mtt) derivatives, respectively, while the threonine was protected its tert-butyl ether. Deprotection of 12 was then achieved with HBr/acetic acid in TFA, 1,2-ethanedithiol to prevent disulfide bond formation, and a "cocktail" of carbocation scavengers (phenol, pentamethylbenzene, triisopropylsilane) at room temperature. The final peptide 13 was purified by reverse-phase HPLC. Both high-field (600 MHz) $^1$H NMR at two different temperatures and amino acid analysis revealed the correct structure for the hexapeptide.

EXAMPLES

Figure 2:
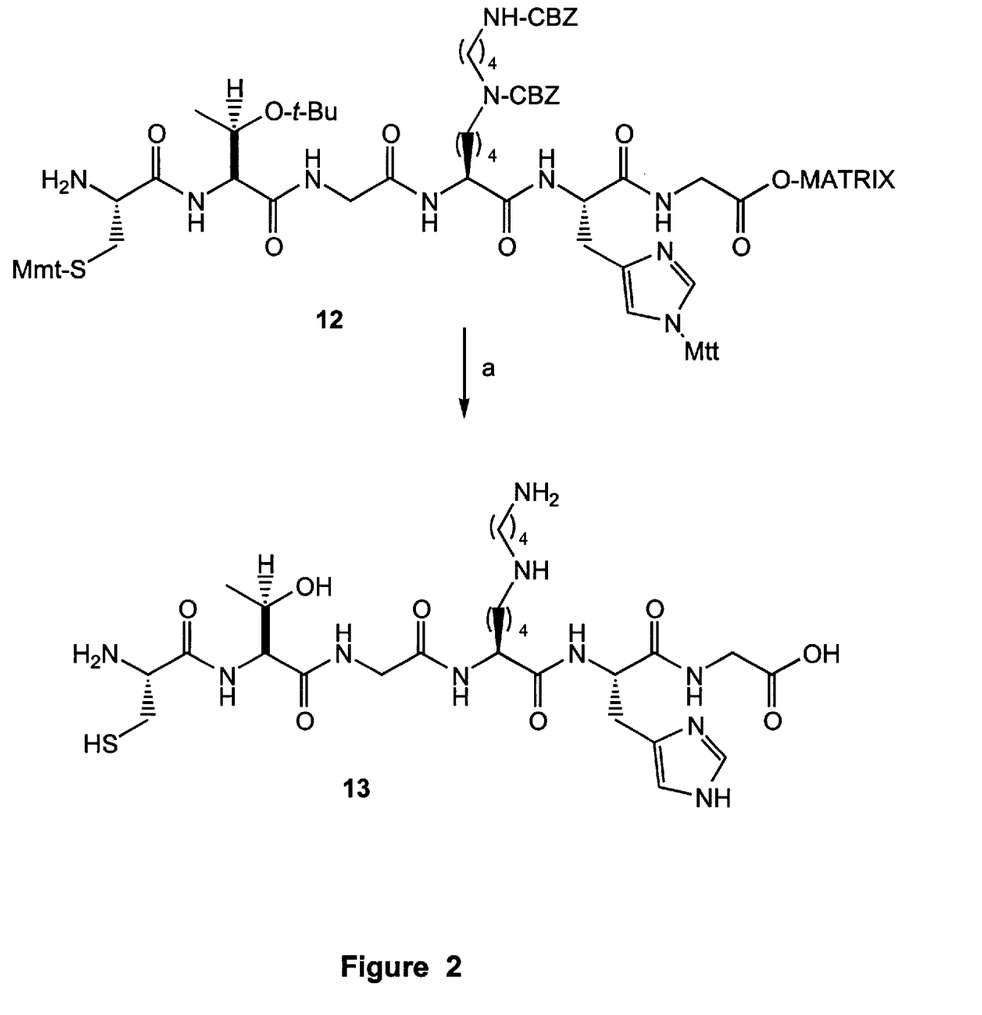
FIG. 2 is a depiction of a polymer-bound synthesis of a deoxyhypusine hexapeptide. Reagents: (a) HBr/acetic acid in TFA, phenol, pentamethylbenzene, triisopropylsilane, 1,2-ethanedithiol.

The invention is illustrated by the following non-limiting examples which refer to the reaction schemes depicted in FIGS. 1–2, wherein $^1$H NMR spectra were recorded at 300 MHz unless otherwise specified; $^{13}$C NMR spectra were recorded at 75 MHz unless otherwise specified; chemical shifts are given in parts per million downfield from an internal tetramethylsilane or sodium 3-(trimethyl-silyl)-propionate standard; coupling constants (J) are given in Hz; mass spectra were carried out on a Kratos MS 80RFA or a Finnigan 4516 MS instrument; optical rotations were run at 589 nm (the Na D-line) on a Perkin-Elmer 341 polarimeter, with c expressed as grams of compound per 100 ml; and melting points were uncorrected. Chemical reagents were purchased from Aldrich, Fluka or Sigma Chemical Co. and used without further purification.

Example 1

Nα-BOC-Nε-CBZ-L-Lysine tert-Butyl Ester (3)

Sodium hydrogen carbonate (2.81 g, 33.47 mmol) in water (75 ml) was added to H-Lys (CBZ)-O-t-Bu hydrochloride (12.00 g, 32.18 mmol) in chloroform (100 ml) and the mixture was stirred at room temperature for 5 minutes under an $N_2$ atmosphere. Di-tert-butyl dicarbonate (7.02 g, 32.18 mmol) in chloroform (50 ml) was added; the mixture was refluxed for 1.5 hours and allowed to cool to room temperature. The layers were separated, the aqueous layer was extracted with chloroform (3×100 ml) and the combined organic layers were dried over magnesium sulfate. Concentration in vacuo followed by flash chromatography (3:1 hexane:ethyl acetate) gave (3) (13.82 g, 98%) as a colorless oil. $^1$H NMR (CDCl$_3$) δ7.30 (s, 5 H), 5.10 (s, 2 H), 4.82 (m, 1 H), 4.18(m, 1 H), 3.20 (m, 2 H), 1.90–1.30 (m, 6 H), 1.48 (s, 9 H), 1.46 (s, 9 H); $^{13}$C NMR (CD$_3$OD) δ173.8, 158.8, 158.1, 138.4, 129.4, 128.9, 128.7, 82.5, 80.4, 67.3, 55.7, 41.4, 32.4, 30.4, 28.7, 28.3, 24.0. HRMS m/z calcd. for $C_{23}H_{37}N_2O_6$ 437.2652, found 437.2643. Anal. calcd. for $C_{23}H_{36}N_2O_6$: C 63.28, H 8.31, N 6.42. Found: C 63.13, H 8.28, N 6.47. $[\alpha]^{27}_D$+5.0°(c=2.00, CHCl$_3$).

Example 2

Nα-BOC-L-Lysine tert-Butyl Ester Hydrochloride (4)

Nα-BOC-Nε-CBZ-L-lysine tert-butyl ester (3) (34.51 g, 79.15 mmol) was dissolved in a mixture of 300 ml absolute EtOH and 1 N HCl (88 ml). Prior to the introduction of $H_2$ gas, 10% Pd—C (2.95 g) was added. After 7 hours, additional catalyst (1.0 g) was added. After 5 hours, the black suspension was filtered through a bed of Celite and washed with EtOH. The filtrate was concentrated, and the residue was dried under high vacuum to give the Nα-BOC-L-lysine tert-butyl ester as its hydrochloride salt (4) (26.59 g, 99%). $^1$H NMR (CD$_3$OD) δ3.95 (dd, 1 H, J=8.8, 5.0), 2.93 (t, 2 H, J=7.7), 1.84–1.60 (m, 6 H), 1.45 (s, 9 H), 1.43 (s, 9 H); $^{13}$C NMR (CD$_3$OD) δ173.5, 158.2, 82.7, 80.5, 79.5, 55.5, 40.6, 32.1, 28.7, 28.3, 23.9. HRMS m/z calcd. for $C_{15}H_{31}N_2O_4$ 303.2284, found 303.2272. $[\alpha]^{26}_{D-}10.1°$(c=1.00, CH$_3$OH).

Example 3

3-Cyanopropanal (5)

A mixture of water (50 mL) and 3-cyanopropionaldehyde diethyl acetal (10.0 g, 63.6 mmol) was refluxed 4 hours under a $N_2$ atmosphere, then distilled at ambient pressure to remove water and ethanol. Glassware utilized for the reflux and initial distillation was acid washed immediately prior to use by submerging in 3 N HCl for 15 min, then rinsing twice with water. The remaining oil was transferred to a dry, short-path distillation apparatus and distilled under reduced pressure to give 5 (4.15 g, 78%): bp 80–82° C. (1.3 mm Hg). $^1$H NMR (CDCl$_3$) 2.63 (t, 2 H, J=7.05), 2.91 (t, 2 H, J=7.05), 9.80 (s, 1 H).

Example 4

(2S)-11-Amino-2-[(tert-Butoxycarbonyl)amino-]7-azaundecanoic Acid tert-Butyl Ester, Diacetate Salt (7)

A solution of 4 (1.00 g, 2.95) in chloroform (30 mL) was extracted with saturated NaHCO$_3$ (2×30 mL), then water (30 mL). The organic layer was dried, evaporated, and dried overnight in vacuo to give the free amine of 4 (749 mg, 84%). This oil was evaporated, and dried overnight in vacuo to give the free amine of 3 (749 mg, 84%). This oil was dissolved in benzene (100 mL) containing 5 (230.5 mg, 2.77 mmol) and activated 3A molecular sieves (20.30 g). The reaction was allowed to stir under argon for 4.5 h, yielding the imine of 6. The solution was filtered and concentrated in vacuo. Under argon, dry THF (100 mL) and $PtO_2$ (150 mg) were added; this was stirred under $H_2$ gas for 17 hours. The black suspension was filtered through Celite to give 6. The filtrate was concentrated, and the residue was immediately dissolved in glacial acetic acid (25 mL). Under argon, $PtO_2$ (152 mg) and 10% Pd—C catalyst (82 mg) were added; the suspension was stirred under $H_2$ gas for 23 h, then filtered through Celite and washed with acetic acid. The filtrate was concentrated in vacuo. Azeotropic removal of acetic acid with toluene provided 7 as a colorless oil (650 mg, 53% calculated from the free amine): $^1$H NMR ($D_2O$) $\delta$1.20–2.00 (m, 10 H), 1.40 (s, 9 H), 1.47 (s, 9 H), 1.97 (s, 6H), 2.97–3.13 (m, 6 H), 3.97 (dd, 1 H, J=9.0, 5.5).

Example 5

(2S)-11-[(Benzyloxycarbonyl)amino]-2-[(tert-butoxycarbonyl)amino]-7-(carbobenzyloxy)-7-azaundecanoic Acid tert-Butyl Ester (8)

Under argon, 7 (556 mg, 1.13 mmol) was dissolved in $H_2O$ (15 mL) and diethyl ether (30 mL). The biphasic mixture was stirred and cooled to 0° C., at which point $KHCO_3$ (1.19 g, 11.9 mmol) was added. Over 20 min, CBZ-ONSu (660.0 mg, 2.648 mmol) was added in five portions. The mixture was allowed to warm to room temperature and stirred for 21 hours. The organic layer was separated, the aqueous layer was washed with ether, and the combined organic layers were dried. Concentration and purification by flash chromatography (2:1 hexane/ethyl acetate) gave 8 (271 mg, 37%) as a colorless oil: $^1$H NMR $\delta$1.20–1.80 (m, 10 H), 1.43 (s, 9 H), 1.44 (s, 9 H), 3.09 (m, 2 H), 3.18–3.32 (m, 4 H), 3.91 (m, 1 H), 5.06 (s, 2 H), 5.09 (s, 2H), 7.26–7.37 (m, 10 H); $^{13}$C NMR ($CDCl_3$) $\delta$22.4, 25.4, 25.8, 27.2, 28.0, 28.3, 32.5, 40.7, 46.5, 47.0, 53.8, 66.6, 66.9, 79.6, 81.7, 127.9, 128.0, 128.5, 136.9, 155.4, 156.1, 156.4, 171.9; HRMS m/z calcd for $C_{35}H_{52}N_3O_8$ 642.3754, found 642.3746. $[\alpha]^{23}_D$=−9.3°(c 1.01, $CH_3OH$).

Example 6

2(S)-Amino-11-[(benzyloxycarbonyl)amino]7-(carbobenzyloxy)-7-azaundecanoic Acid (9)

Under argon, 8 (271 mg, 0.422 mmol) was added to a mixture of trifluoroacetic acid (770 mg, 6.7 mmol), $CH_2Cl_2$ (3.0 mL), and triethylsilane (330 mg, 2.8 mmol); this was stirred at room temperature for 23 hours. The reaction mixture was concentrated; the resultant oil was dissolved in water (5.0 mL) and adjusted to pH 7 with saturated $NaHCO_3$ solution. This solution was then concentrated; the residue was purified by chromatography on a C-18 column (30% acetone/water, followed by 55% acetone/water) to give 9 (137 mg, 67%) as a colorless oil: $^1$H NMR (19.7° C.) $\delta$1.30–1.66 (m, 8 H), 1.78 (m, 2 H), 3.09 (m, 2 H), 3.20–3.33 (m, 4 H), 3.45 (m, 1 H), 5.05(s, 2H), 5.09 (s, 2 H), 7.26–7.37 (m, 10 H); HRMS m/z calcd for $C_{26}H_{36}N_3O_6$ 486.2604, found 486.2614.

Example 7

11-[(Benzyloxycarbonyl)amino]-7-(carbobenzyloxy)-2(S)-[(9-fluorenylmethoxycarbonyl)amino]-7-azaundecanoic Acid (10)

A solution of 9-fluorenylmethyl N-succinimidyl carbonate (143 mg, 0.42 mmol) in DMF (1.60 mL) was added to a solution of 9 (135 mg, 0.278 mmol) in 9% $Na_2CO_3$ (655.9 mg, 0.557 mmol) at 0° C. and stirred at room temperature for 21 hours under argon. The pH was adjusted to 7.0 with 0.1 N HCl. The mixture was concentrated to an oil and purified by flash chromatography ($CHCl_3$, then 95% $CHCl_3$MeOH) to give 10 (115 mg, 58%) as a colorless oil: $^1$H NMR (19.2° C.) $\delta$1.22–1.92 (m, 10 H), 3.08 (m, 2 H), 3.16–3.30 (m, 4 H), 4.12 (m, 1 H), 4.21 (t, 1 H, J=6.9), 4.30–4.45 (m, 2 H), 5.04(s, 2H), 5.08 (s, 2 H), 7.22–7.42 (m, 14 H), 7.66 (m, 2 H), 7.78 (d, 2 H, J=7.5); HRMS m/z calcd for $C_{41}H_{46}N_3O_8$ 708.3285, found 708.3284. $[\delta]^{22}_D$=+9.3°(c 1.00, $CHCl_3$).

Example 8

(S)-Deoxyhypusine Dihydrochloride (11).

Under argon, phenol (270 mg), pentamethylbenzene (250 mg), and ester 10 (53 mg, 75 $\mu$mol) were dissolved in trifluoroacetic acid (5 mL) at 0° C. With vigorous stirring, triisopropylsilane (200 $\mu$L) and 30% HBR/acetic acid were added, and the solution was allowed to stir 5 minutes before being warmed to room temperature and stirred for an additional 55 minutes. The crude product was purified by flash chromatography [1:2:1 $CH_2Cl_2$/MeOH/$NH_3$(aq)], Kieselgel 60, concentrated, dissolved in 1 mL $H_2O$, and adjusted to pH=4.5 with 0.1 N HCl. Concentration and recrystallization from 1:9:15 $H_2O$/MeOH/$Et_2O$ gave 11 as the dihydrochloride salt (6.6 mg, 30%): $^1$H NMR ($D_2O$) $\delta$1.53 (m, 2 H), 1.76 (m, 6 H), 1.97 (m, 2 H), 3.01–3.15 (m, 6 H), 3.98(t, 1 H, J=6.3). HRMS m/z calcd for $C_{10}H_{24}N_3O_2$ 218.1868, found 218.1900. $[\delta]^{21}_D$=+17.0° (c 0.44, 6 N HCl).

Example 9

Compound 12

Synthesis of the polymer-bound, protected peptide 12, was performed on an Applied Biosystems 432A synthesizer with a 2-chlorotrityl resin at room temperature. Appropriately protected amino acids and the deoxyhypusine reagent 10 were used.

Example 10

Cys-Thr-Gly-deoxyhypusine-His-Gly (13)

The polymer-bound peptide 12 (87.4 mg), phenol (250 mg), and pentamethylbenzene (2.50 mg) were dissolved in degassed TFA (5.0 mL) at 0° C. Triisopropylsilane (100 $\mu$L), 1,2-ethanedithiol (100 $\mu$L), and saturated HBr in acetic acid solution (200 $\mu$) were added under an argon atmosphere. The solution was stirred at room temperature for one hour and was concentrated under reduced pressure. The residue was dissolved in 10% acetic acid (10 mL) and extracted with methyl tert-butyl ether (3×25 mL). The aqueous layer was concentrated in vacuo, and the residue was purified on a preparative HPLC (solvent systems A, aqueous 0.1% TFA; and B, 0.1% TFA in $CH_3CN$; linear gradient of 0–20% B in 85 min; flow rate 12 ml/min; detection at 214 nm; retention time=13.7 min) using a C-18 reverse phase column (Vydac Protein & Peptide C-18) to give 13 as a colorless oil (8.0 mg, 28%, calculated as tetrakis-trifluoroacetate salt): $^1$H NMR (600 MHz, 6.0° C.) $\delta$1.26 (d, 3 H, J=6.2), 1.38 (m, 2 H), 1.63–1.81 (m, 8 H), 2.98–3.11 (m, 7 H), 3.15 (dd, 1 H, J=14.9, 5.6), 3.19 (dd, H,J=15.4, 8.1), 3.31 (dd,1 H, J=15.4; 6,2), 3.94–4.06 (m, 4 H), 4.23 (m, 1 H), 4.30 (m, 1H), 4.35 (m, 1 H), 4.42 (d, 1 H, J=4.8), 4.77 (m, 1 H), 7.32 (s, 1 H), 8.64 (s, 1 H). Amino acid analysis: Thr 0.65, Gly 2.34, His 1.02.

I claim:

1. A method of synthesizing a deoxyhypusine derivative having the formula:

(1)

wherein: $Q_1$ and $Q_2$ may be the same or different and are amino protective groups and $Q_3$ is an amino protective group which is orthogonal to $Q_1$ and $Q_2$, comprising:

a. providing an ester of $N_\epsilon$-, $N_\alpha$-diprotected lysine, said ester having the formula:

(a)

wherein prot and prot' are mutually orthogonal amino-protective groups and R is the residue of an esterifying alcohol which is orthogonal with respect to prot and prot', b. removing prot from $N_\epsilon$ of (a) and converting the product to a compound of the formula:

(b)

c. condensing (b) with 3-cyanopropanal and reducing the intermediate imine to a cyanide of the formula:

(c)

d. reducing (c) to produce a triamine of the formula:

(d)

e. protecting the free amino groups of (d) to produce an ester of the formula:

f. removing R and prot' from (e) to produce a compound of the formula:

and g. acylating the free amino group to produce the deoxyhypusine derivative (1).

2. The method of claim 1 wherein ester (a) is provided by esterifying the $N_\epsilon$-,$N_\alpha$-diprotected L-lysine, wherein prot is carbobenzyloxy.

3. The method of claim 1 wherein prot' is BOC.

4. The method of claim 1 wherein R is t-butyl.

5. The method of claim 1 wherein prot is removed from (a) by hydrogenation to give (b).

6. The method of claim 5 wherein said hydrogenation is effected in the presence of $PtO_2$.

7. The method of claim 1 wherein the CN group of (c) is converted to an amino group by catalytic hydrogenation.

8. The method of claim 7 wherein said hydrogenation is conducted in the presence of a mixture of palladium-C and $PtO_2$.

9. The method of claim 1 wherein the free amino groups of (d) are acylated with a reactive carbobenzyloxycarboxylic acid derivative to produce (e) wherein $Q_1$ and $Q_2$ are each carbobenzyloxy groups.

10. The method of claim 9 wherein said reactive carbobenzyloxycarboxylic acid derivative is N-(benzylcarbonxyloxy)succinimide.

11. The method of claim 1 wherein R and prot' are removed by reaction with trifluoroacetic acid.

12. The method of claim 11 wherein said reaction with trifluoroacetic acid is conducted in the presence of triethylsilane.

13. The method of claim 1 wherein the free amino group of (f) is acylated with 9-fluorenylmethyl-N-succinimidyl carbonate to produce a hypusine reagent wherein $Q_3$ is fluorenylmethoxycarbonyl.

14. A peptide of formula:
X-L-Ser-L-LYS-L-Thr-Gly-deoxyHpu-L-His-Gly-L-His-L-Ala-L-Lys-Y wherein deoxyHpu is a deoxyhypusine residue, X and Y are peptide residues each independently comprising from zero to about 8 amino acids.

15. The peptide of claim 14, wherein said peptide is L-Ser-L-Thr-L-Ser-L-Lys-L-Thr-Gly-deoxyhypusine-L-His-Gly-L-His-L-Ala-L-Lys (SEQ ID NO: 2).

16. A peptide of the formula L-Cys-L-Thr-Gly-deoxyhypusine-L-His-Gly (SEQ ID NO: 3).

17. A peptide selected from the group consisting of deoxyhypusine-L-His-Gly, L-Thr-Gly-deoxyhypusine-L-His-Gly (SEQ ID NO: 4), and L-Lys-L-Thr-Gly-deoxyhypusine-L-His-Gly (SEQ ID NO: 5).

* * * * *